United States Patent [19]

Bouillon et al.

[11] 4,381,294
[45] Apr. 26, 1983

[54] PROCESS FOR REINFORCING FRAGILE OR BRITTLE NAILS AND A COMPOSITION CONTAINING A CATIONIC POLYMER FOR USE IN SAID PROCESS

[75] Inventors: Claude Bouillon, Eaubonne; Jean-Louis Abegg; Constantin Koulbanis, both of Paris; Patrick Darmenton, Villejuif, all of France

[73] Assignee: Societe Anonyme dite: L'OREAL, Paris, France

[21] Appl. No.: 98,330

[22] Filed: Nov. 27, 1979

[30] Foreign Application Priority Data

Dec. 1, 1978 [FR] France ............................ 78 33965

[51] Int. Cl.³ ............................................. A61K 7/04
[52] U.S. Cl. ...................................... 424/61; 424/78; 424/81; 424/168; 424/359
[58] Field of Search ............................................ 424/61

[56] References Cited

U.S. PATENT DOCUMENTS

| 3,749,769 | 7/1973 | Sugiyama et al. | 424/61 |
| 3,860,700 | 1/1975 | Viout et al. | 424/61 |
| 3,937,802 | 2/1976 | Fujimoto et al. | 424/61 |
| 4,097,589 | 6/1978 | Shansky | 424/61 |
| 4,240,450 | 12/1980 | Grollier et al. | 424/61 |

FOREIGN PATENT DOCUMENTS

| 2047129 | 9/1970 | Fed. Rep. of Germany | 424/61 |
| 1485602 | 5/1967 | France | 424/61 |

*Primary Examiner*—Dale R. Ore
*Attorney, Agent, or Firm*—Cushman, Darby & Cushman

[57] ABSTRACT

A process for reinforcing fragile or brittle nails comprises applying to the nail surface a composition containing a cationic polymer.

24 Claims, No Drawings

PROCESS FOR REINFORCING FRAGILE OR BRITTLE NAILS AND A COMPOSITION CONTAINING A CATIONIC POLYMER FOR USE IN SAID PROCESS

The present invention relates to a process for reinforcing fragile and/or brittle nails using certain cationic polymers.

The present invention also relates to a new cosmetic composition for the care of nails, said composition containing these cationic polymers.

BACKGROUND OF THE INVENTION

It is well-known that for various reasons the nails, and, principally women's nails, often exhibit surface unevenness, have a marked tendency to crack and to split, exhibit transitory or chronic tarnishing, exhibit partial or extensive softening of the whole of the body of the nail and, in a general manner, have an abnormal fragility.

Thus, the nails exhibit an unaesthetic and awkward appearance and are a source of inconvenience and multiple unpleasantness.

In order to reinforce the nails and also to protect them vis-a-vis an attack by external agents, it has previously been recommended to use various different methods which employ compositions based either on protein crosslinking agents so as to reinforce the keratinic system of the nails, such crosslinking agents including, for example, formol or certain of its derivatives, such as bis-(hydroxymethyl) ethylene thiourea, or on agents which function essentially as nutratives such as, for example, fatty acids, cystine, cholesterol, S-carboxymethylcysteine or even collagen extracts.

The use of such crosslinking agents or nutrative agents do not provide, however, acceptable results. Further, the use of these types of agents create certain disadvantages. In particular, products based on formol or its derivatives can cause certain allergic reactions.

GENERAL DESCRIPTION OF THE INVENTION

It has now been found that by using only certain suitably selected classes of cationic polymers, it is possible to obtain a remarkable hardening of the nails.

In effect, the cationic polymers used in accordance with the presnt invention exhibit a very great affinity vis-a-vis the nail and, moreover, they possess good film-forming properties which imparts to the nail surface very effective protection against the harmful action of numerous external agents and at the same time preserves the nails from risks of being altered due to their fragility.

The cationic polymers used in the process in accordance with the present invention harden the nails without, however, rendering them brittle.

DETAILED DESCRIPTION OF THE INVENTION

The present invention thus relates to a process for reinforcing fragile and/or brittle nails comprising applying to the nail surface, in a conventional manner, a composition containing at least one cationic polymer selected from the group consisting of (1) a crosslinked polyamino-polyamide having the formula $$\text{\textendash}OC\text{\textendash}R\text{\textendash}CO\text{\textendash}Z\text{\textendash} \quad (I)$$

wherein
R represents a radical selected from the group consisting of (i) $-\mathrm{C_6H_4}-$ (para-phenylene)

(ii) $-(CH_2)_4-$ (iii) $-(CH_2)_2-NH-(CH_2)_2-NH-(CH_2)_2-$ (iv) $-\underset{\underset{CH_3}{|}}{CH}-CH_2-NH-(CH_2)_2-NH-CH_2-\underset{\underset{CH_3}{|}}{CH}-$ and (v) a bis-succinimide-ethylenediamine type radical and
Z represents
(a) in an amount ranging from 60 to 100 mole percent, the radical:

$$-[NH-(CH_2)_x-NH]_n-$$

wherein $x=2$ and $n=2$ or 3, or $x=3$ and $n=2$, (b) in an amount ranging from 0 to 40 mole percent, a radical selected from the group consisting of
(a') $-NH-(CH_2)_x-NH-_n$ wherein $x=2$ and $n=1$, and
(b') a piperazine ring $-N\underset{\phantom{xx}}{\phantom{xx}}N-$, and
(c) in an amount ranging from 0 to 20 mole percent, the radical, $-NH-(CH_2)_6-NH-$, the crosslinking being effected with the aid of an agent selected from the group consisting of epihalohydrin, diepoxide, dianhydride and bis-unsaturated derivative;

(2) adipic acid-dimethylaminohydroxypropyldiethylenetriamine polymers having a nitrogen content ranging from 17.0–18.0 weight percent, and a viscosity, measured in a 30% weight aqueous solution, of 350–800 centipoises at 20° C. (determined by a Brookfield viscosimeter using a No. 3 spindle at 30 t/mn);

(3) polymers obtained by the reaction of a polyalkylene-polyamine having two primary amine groups and at least one secondary amine group with a discarboxylic acid selected from the group consisting of diglycolic acid and saturated aliphatic acids having from 3 to 8 carbon atoms, the molar ratio of the polyalkylene-polyamine to the dicarboxylic acid being about 0.8:1 to 1.4:1 and finally by reaction of the resulting polyaminoamide with epichlorohydrin in a molar ratio of epichlorohydrin to the secondary amine group of said polyaminoamide from 0.5:1 to 1.8:1;

(4) cyclopolymers selected from the group consisting of (i) homopolymers of dimethyldiallyl ammonium chloride having a molecular weight lower than 100,000, and
(ii) cyclopolymers of dimethyldiallyl ammonium chloride and acrylamide having a molecular weight greater than 500,000.

After applying the nail reinforcing composition of this invention to the nail surface, the composition is permitted to react for a time varying from a few minutes to several hours. So as to obtain particularly significant results, it is preferable to apply the composition in the evening and let it act overnight. Particularly significant results are obtained after daily treatment of the nails from 3-8 weeks, the resulting hardness being dependent on the initial state of the nails.

In accordance with a preferred process of the present invention there is employed a composition having a concentration of the cationic polymer, such as those enumerated above, between 0.1 and 2 weight percent and, preferably, between 0.5 and 1 weight percent, based on the total weight of the composition.

The crosslinked polyamino-polyamides, such as defined above in (1), are described in French Pat. No. 2,252,840.

The adipic acid-dimethylaminohydroxypropyldiethylenetriamine copolymers, such as defined in (2) above, are described in French Pat. No. 1,583,363 to Sandoz. In accordance with a particular embodiment of the present invention, there is employed, preferably, a copolymer of this type known under the commercial name of "Cartaretine F 4" sold by Sandoz.

Copolymers, such as defined above under (3), are described in U.S. Pat. Nos. 3,227,615 and 2,961,347. There are preferably employed those copolymers sold under the commercial names of "Hercosett 57", "Delsette 101" or "Delsette P.D. 170" sold by Hercules Inc.

The homopolymers and copolymers, such as defined above under (4), are described in French Pat. No. 2,080,759 and its certificate of addition No. 2,190,406. Preferably, the homopolymers sold under the commercial name of "Merquat 100" or the copolymer sold under the commercial name of "Merquat 550", sold by Merck are employed.

In accordance with a preferred implementation of the process of the present invention, there is employed a composition containing at least one cationic polymer, such as enumerated above, in combination with at least one other cationic polymer, hereinafter termed an additional cationic polymer and in this embodiment this additional cationic polymer is present in an amount between 0.1 and 3 weight percent.

In effect, it has been noted that when such a mixture is applied to the nails, it is possible to obtain a better reinforcement of the keratin of the nails although it has also been noted that the additional cationic polymers, alone, have no apparent nail reinforcing characteristics.

Representative additional cationic polymers useful in the compositions of the present invention to reinforce the nails, include, for instance:

(A) copolymers having the following formula:

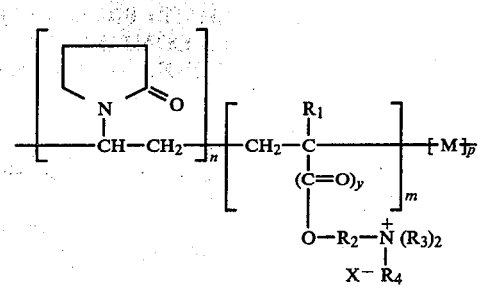

wherein
$R_1$ represents H or $CH_3$,
$R_2$ is $-CH_2-CHOH-CH_2-$ or $C_xH_{2x}-$ wherein x is 2-18,
$R_3$ represents $-CH_3$, $-C_2H_5$ and X is Cl, Br, I, ½ $SO_4$, $HSO_4$ or $CH_3SO_3$,
y is 0 or 1,
M is a unit of a polymerizable vinyl monomer,
n represents from 20 to 99 and, preferably, from 40 to 90 mole percent,
m represents from 1 to 80 and, preferably, from 5 to 40 mole percent, and
p represents from 0 to 50 mole percent, with n+m+p being equal to 100 mole percent.

These copolymers have a molecular weight between about 100,000 and 1,000,000 and are described in French Pat. No. 2,077,143. Preferably there is employed the compound known under the commercial name of "Gafquat 755" sold by General Anilin;

(B) Graft cationic copolymers, optionally crosslinked, resulting from the copolymerization of:
(a) from 3 to 95 weight percent of at least one cosmetic monomer selected from the group consisting of vinyl acetate, vinyl propionate, methyl methacrylate, stearyl methacrylate, lauryl methacrylate, ethylvinylether, cetylvinylether, stearylvinylether, 1-hexene, octadecene, N-vinylpyrrolidone and N,N-diethylaminoethyl mono maleate, maleic anhydride and diethyl maleate,
(b) from 3 to 95 weight percent of dimethylaminoethyl methacrylate,
(c) from 2 to 50 weight percent and, preferably, from 5 to 30 weight percent of polyethylene glycol, and optionally,
(d) from 0.1 to 8 weight percent, relative to the weight of monomers (a), (b) and (c), of a crosslinking agent selected from the group consisting of ethylene glycol dimethacrylate, diallylphthalate, divinylbenzene, tetraallyloxyethane and polyallylsucrose having from 2-5 allyl groups per mole of sucrose.

The graft and crosslinked cationic copolymers are described in French Pat. No. 2,189,434 (73.22222). These copolymers have a molecular weight of 10,000 to 1,000,000 and, preferably, from 15,000 to 500,000.

A representative useful graft cationic copolymer which is, however, not crosslinked, is one resulting from the polymerization of:
(a) 50 weight percent N-vinylpyrrolidone,
(b) 41 weight percent quaternized dimethylaminoethyl methacrylate and
(c) 8 weight percent polyethylene glycol;

(C) The quaternary derivatives of cellulose ether such as those described in French Pat. No. 1,492,597 and, in particular, the product known under the commercial name of "JR 400" and sold by Union Carbide;

(D) Polyquaternary polymers of the formula

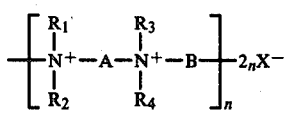

wherein $R_1$, $R_3$, $R_3$ and $R_4$, each independently, represent aliphatic, alicyclic or arylaliphatic radicals containing a maximum of 20 carbon atoms or a lower hydroxyaliphatic radical, or the combinations of $R_1$ and $R_2$, and of $R_3$ and $R_4$, both or separately constitute with the nitrogen atoms to which each are attached, heterocycles containing, optionally, a second heteroatom other than nitrogen, or $R_1$, $R_2$, $R_3$ and $R_4$ represent

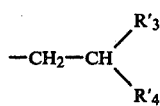

wherein $R'_3$ represents hydrogen or lower alkyl and $R'_4$ represents

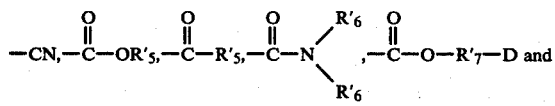

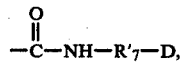

wherein $R'_5$ represents lower alkyl, $R'_6$ represents hydrogen or lower alkyl, $R'_7$ represents alkylene and D represents a quaternary ammonium group, A and B represent polymethylene groups containing from 2 to 20 carbon atoms which groups can be linear or branched, saturated or unsaturated and can contain, interposed in the principal chain thereof one or more aromatic rings or one or more —$CH_2$—Y—$CH_2$— groups wherein Y represents —O—, —S—,

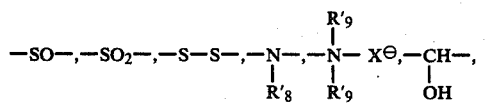

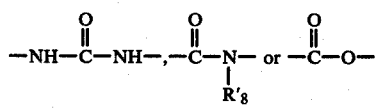

wherein $R'_8$ represents hydrogen or lower alkyl, $R'_9$ represents lower alkyl or indeed A and $R_1$ and $R_3$ form with the two nitrogen atoms to which they are attached, a piperazine ring, $X^\ominus$ is an anion derived from a mineral or organic acid, and n is a number such that the molecular mass is between 1,000 and 100,000.

Polymers of this type are described in French Patent Nos. 2,320,330 and 2,270,846 as well as in U.S. Pat. Nos. 2,273,780; 2,375,853; 2,388,614; 2,454,457; 3,206,462; 2,262,002; 2,271,378; 3,874,870; 4,001,432; 3,929,990; 3,966,904 and 4,005,193.

Among the polymers of this type there are, preferably employed, those having the following units, wherein Hal is Cl or Br:

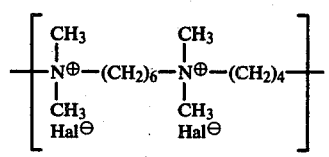

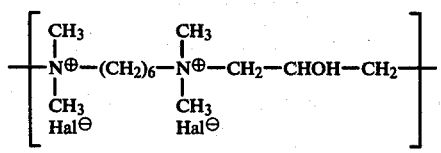

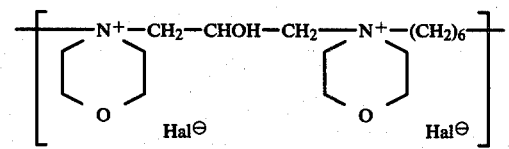

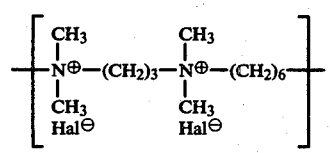

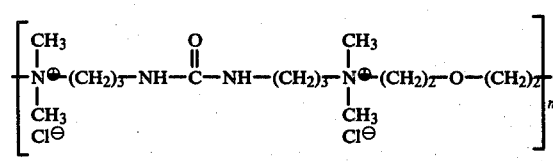

wherein n is equal to about 6. This latter polymer is sold under the name of "Mirapol A15" by Miranol, as well as the poly(dimethyl butenyl ammonium chloride)-α,ω-bis (triethanolammonium chloride) sold under the commercial name "Onamer M" by Onyx Chemical; and (E) polyquaternary polymers of the formula

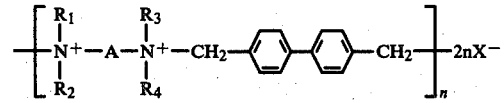

wherein the $R_1$, $R_2$, $R_3$, $R_4$ radicals, n and X have the same meanings as those given above for polymers (D), and Polymers (E) are described, in particular, in French Pat. No. 2,336,434.

Moreover, polymers of the same type are also described in U.S. Pat. Nos. 4,025,617; 4,025,627; 4,025,653; 4,026,945 and 4,027,020.

The present invention also relates to certain compositions for use in the process of treating nails, such as defined above and, in particular, to emulsions of the oil-in-water type and to dispersions in a mixture of fatty alcohols.

The oil-in-water emulsions according to the present invention are preferably obtained starting with paraffin oil and polyglycerol alkylethers. They contain, in general, between 5 and 20 weight percent paraffin oil.

The polyglycerol alkylethers can be selected from the compounds described in French Pat. No. 1,477,048 and are preferably used in an amount of 2 to 20 weight percent based on the total weight of the composition.

These polyglycerol alkylethers have the following formula:

$$RO-[C_2H_3O(CH_2OH)]_{\overline{n}}H$$

wherein R represents a lipophile chain and, principally, a linear or branched alkyl or alkenyl radical having from 8–22 carbon atoms or a mixture of such radicals, n being a statistical number lower than or equal to 10.

The dispersions in water, in accordance with the present invention, are obtained with the aid of at least one fatty alcohol such as, for example, cetyl alcohol, stearyl alcohol or a mixture thereof, said fatty alcohol being able to be in a form partially oxyethylenated with 20–50 moles of ethylene oxide.

The fatty alcohol concentration in the dispersions is generally between 1 and 10 weight percent based on the total weight of the composition. When cetyl alcohol, stearyl alcohol or cetyl stearyl alcohol (Lanette wax) is used, the mixture can be emulsified by means of a non-ionic or cationic surfactant.

On the other hand, when partially oxyethylenated fatty alcohol, such as, for example, Sipol wax (30% cetyl alcohol/70% stearyl alcohol oxyethylenated with 33 moles of ethylene oxide) is used, this material is self-emulsifiable and thus it is not necessary to use an additional surfactant with it.

Representative surfactants which can be used in the compositions of this invention include the fatty esters of sorbitan polyoxyethylenated with 20–80 moles of ethylene oxide, such as the laurate, oleate, palmitate or stearate.

There can also be used as a surfactant, a polyoxyethylenated alkylphenol, such as the product known under the commercial name of "Triton X 100" (isooctylphenol polyoxyethylenated with 10 moles of ethylene oxide) and sold by Rohm and Haas.

The compositions of the present invention can also contain a certain number of additives conventionally employed in cosmetics, such as plasticizing agents selected from polyethylene glycol having a molecular weight between 200 and 1,500; isopropyl myristate; 2-octyl dodecanol; butyl stearate; as well as certain resins, such as polyvinylpyrrolidones, polyvinyl alcohols, gum arabic, hydroxyalkyl celluloses or even the terpolymer vinylacetate/acrylates sold under the commercial name "Resyn 2261" and sold by National Starch and having a viscosity of 900 cps and a particle size of 0.2μ.

However, there can also be used in the compositions of the present invention, in the form of oil-in-water emulsions or dispersions, various conventional adjuvants such as alcohols and, principally, propylene glycol, glycerol and sorbitol, antioxidants, dyes, pigments, solar filters, proteins, vitamins, nonsaponifiables derived from vegetable oils, as well as perfumes.

These compositions, in the form of oil-in-water emulsions or dispersions such as those defined above, are particularly appropriate so as to obtain excellent results in the process of treating nails.

The following non-limiting Examples are given to illustrate the process of reinforcing fragile and/or brittle nails using various compositions in accordance with the present invention.

EXAMPLE 1

To reinforce fragile and/or brittle nails, there is applied in a conventional manner to the nail surface an oil-in-water emulsion comprising a mixture of the following components:

| | |
|---|---|
| Polyglycerol alkyl ethers: | |
| $C_{16}H_{33}/C_{18}H_{37}-O-[C_2H_3O(CH_2OH)]_{\overline{16}}H$ | } 20 g |
| $C_{16}H_{33}/C_{18}H_{37}-O-[C_2H_3O(CH_2OH)]_{\overline{7}}H$ | |
| Paraffin oil | 9.6 g |
| Polyaminoamide (adipic acid + diethylene triamine) crosslinked with epichlorohydrin (11 moles of crosslinking agent/100 amine groups) | 0.5 g |
| "Gafquat 755" | 1.5 g |
| Perfume | 0.2 g |
| Demineralized water, sufficient for | 100 g |

The composition is left to act overnight on the nails and, after a similar daily treatment for about 4 weeks, there is noted a reinforcement of the keratin of the nail. Further, the film deposited on the nail protects the nails from external attack.

To reinforce fragile and brittle nails, there is applied on the nail surface the following oil-in-water emulsions:

EXAMPLE 2

| | |
|---|---|
| Polyglycerol alkylethers: | |
| $C_{16}H_{33}/C_{18}H_{37}-O-[C_2H_3O(CH_2OH)]_{\overline{16}}H$ | } 6.5 g |
| $C_{16}H_{33}/C_{18}H_{37}-O-[C_2H_3O(CH_2OH)]_{\overline{7}}H$ | |
| Paraffin oil | 10 g |
| Polyaminoamide (adipic acid + diethylene triamine) crosslinked with epichlorohydrin (11 moles of crosslinking agent/100 amine groups) | 0.1 g |
| "Gafquat 755" | 2 g |
| Perfume | 0.1 g |
| Demineralized water, sufficient for | 100 g |

EXAMPLE 3

| | |
|---|---|
| Polyglycerol alkylethers: | |
| $C_{16}H_{33}/C_{18}H_{37}-O-[C_2H_3O(CH_2OH)]_{\overline{16}}H$ | } 3 g |
| $C_{16}H_{33}/C_{18}H_{37}-O-[C_2H_3O(CH_2OH)]_{\overline{7}}H$ | |
| Paraffin oil | 8 g |
| "Merquat 550" | 0.2 g |
| Copolymer of 50.6% N—vinylpyrrolidone/ 41.25% dimethylaminoethyl methacrylate quaternized with dimethyl sulfate/ 8.15% polyethylene glycol | 1.5 g |
| Perfume | 0.2 g |
| Demineralized water, sufficient for | 100 g |

EXAMPLE 4

| | |
|---|---|
| Polyglycerol alkylethers: | |
| $C_{16}H_{33}/C_{18}H_{37}-O-[C_2H_3O(CH_2OH)]_{\overline{16}}H$ | } 10 g |
| $C_{16}H_{33}/C_{18}H_{37}-O-[C_2H_3O(CH_2OH)]_{\overline{7}}H$ | |
| Paraffin oil | 16 g |
| "Merquat 100" | 2 g |
| Butylhydroxy toluene | 0.05 g |

| | |
|---|---|
| Butylhydroxy anisole | 0.05 g |
| Perfume | 0.15 g |
| Demineralized water, sufficient for | 100 g |

EXAMPLE 5

| | |
|---|---|
| Polyglycerol alkylethers: | |
| $C_{16}H_{33}/C_{18}H_{37}-O-(C_2H_3O(CH_2OH))_{16}H$ | |
| $C_{16}H_{33}/C_{18}H_{37}-O-(C_2H_3O(CH_2OH))_{12}H$ | 6 g |
| Paraffin oil | 9 g |
| "Cartaretine F 4" | 0.5 g |
| Perfume | 0.1 g |
| Demineralized water, sufficient for | 100 g |

EXAMPLE 6

| | |
|---|---|
| Polyglycerol alkylethers: | |
| $C_{16}H_{33}/C_{18}H_{37}-O-(C_2H_3O(CH_2OH))_{16}H$ | |
| $C_{16}H_{33}/C_{18}H_{37}-O-(C_2H_3O(CH_2OH))_{12}H$ | 15 g |
| Paraffin oil | 20 g |
| "Delsette 101" | 0.8 g |
| Perfume | 0.2 g |
| Demineralized water, sufficient for | 100 g |

EXAMPLE 7

| | |
|---|---|
| Polyglycerol alkylethers: | |
| $C_{16}H_{33}/C_{18}H_{37}-O-(C_2H_3O(CH_2OH))_{16}H$ | |
| $C_{16}H_{33}/C_{18}H_{37}-O-(C_2H_3O(CH_2OHO))_{12}H$ | 6 g |
| Paraffin oil | 9 g |
| Polyaminoamide (adipic acid + diethylene triamine) crosslinked with epichlorohydrin (11 moles of crosslinking agent/100 amine groups) | 0.5 g |
| "Gafquat 755" | 1.5 g |
| Perfume | 0.2 g |
| Water, sufficient for | 100 g |

After leaving compositions Nos. 2-7 above to act on the nail overnight and by repeating this operation daily for about 3 weeks, it is observed that the nails are less brittle and are more resistant to impact.

To reinforce fragile and/or brittle nails, there is applied, in a conventional manner, to the nail surface the following dispersions:

EXAMPLE 8

| | |
|---|---|
| Sipol wax | 4 g |
| "Hercosett 57" | 0.5 g |
| Isorpopyl myristate | 2 g |
| Glycerol | 3 g |
| Perfume | 0.3 g |
| Demineralized water, sufficient for | 100 g |

EXAMPLE 9

| | |
|---|---|
| Sipol wax | 5 g |
| Cetyl alcohol | 1 g |
| Polyethylene glycol 300 | 1.5 g |
| "Delsette 101" | 0.4 g |
| "Onamer M" [poly-(dimethyl-butenylammonium chloride)-α, ω-bis (triethanolammonium chloride), MW = 1,000-1,200; viscosity: 100 cps] | 0.8 g |
| Butylhydroxy toluene | 0.025 g |
| Butylhydroxy anisole | 0.025 g |
| Glycerol | 4 g |
| Perfume | 0.3 g |
| Demineralized water | 100 g |

EXAMPLE 10

| | |
|---|---|
| Lanette wax | 10 g |
| Myristic alcohol | 5 g |
| Glycerine | 5 g |
| Nonsaponifiables of lucern | 0.2 g |
| Sorbitan monolaurate polyoxyethylenated with 20 moles of ethylene oxide | 0.2 g |
| Polyaminoamide (adipic acid + diethylene triamine) crosslinked with epichlorohydrin | 0.6 g |

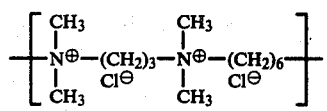

1 g

| | |
|---|---|
| Perfume | 0.2 g |
| Demineralized water, sufficient for | 100 g |

EXAMPLE 11

| | |
|---|---|
| Cetyl-stearyl alcohol oxyethylenated with 25 moles of ethylene oxide | 5 g |
| Cetyl alcohol | 1 g |
| 2-octyl dodecanol | 10 g |
| "Cartaretine F 4" | 1 g |

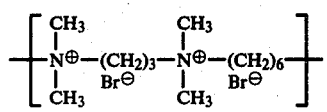

0.5 g

| | |
|---|---|
| Perfume | 0.2 g |
| Water, sufficient for | 100 g |

After leaving the compositions Nos. 8-11 to act on the nails, it is observed that after a daily treatment for a few weeks, the nails exhibit an improved surface condition and have much less tendency to crack or split.

What is claimed is:

1. A process for reinforcing fragile or brittle nails comprising applying to the nail surface an effective amount of a composition consisting essentially of at least one cationic polymer selected from the group consisting of (1) a crosslinked polyamino-polyamide having the formula

wherein

R represents a radical selected from the group consisting of

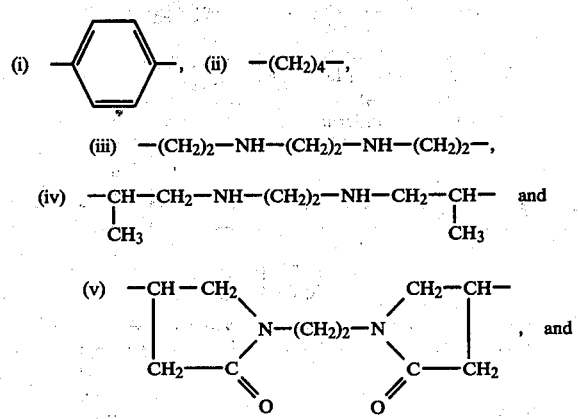

represents:
(a) in an amount from 60 to 100 mole percent, the radical, $-NH-(CH_2)_x-NH-_n$ wherein $x=2$ and $n=2$ or 3, or $x=3$ and $n=2$,
(b) in an amount from 0 to 40 mole percent, a radical selected from the group consisting of:
(a') $-NH-[(CH_2)_x-NH-]_n$ wherein $x=2$ and $n=1$, and (b')

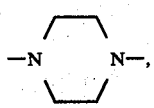

and (c) in an amount from 0 to 20 mole percent, the radical, $-NH-(CH_2)_6-NH-$, crosslinked with a crosslinking agent selected from the group consisting of an epihalohydrin, a diepoxide, a dianhydride and a bis-unsaturated derivative;
(2) an adipic acid-dimethylaminohydroxypropyl diethylenetriamine polymer having a nitrogen content of 17.0–18.0 weight percent thereof, and a viscosity measured in a 30% aqueous solution of 350–800 centipoises at 20° C.;
(3) a polymer obtained by the reaction of a polyalkylenepolyamine having two primary amine groups and at least one secondary amine group with a dicarboxylic acid selected from the group consisting of diglycolic acid and a saturated aliphatic acid having 3–8 carbon atoms, the molar ratio of said polyalkylene polyamine to said dicarboxylic acid being about 0.8:1 to 1.4:1 and by the reaction of the resulting polyaminoamide with epichlorohydrin, the molar ratio of said epichlorohydrin to the secondary amine group of said polyaminoamide being from 0.5:1 to 1.8:1; and
(4) a cyclopolymer selected from the group consisting of
(i) a homopolymer of dimethylammonium chloride having a molecular weight lower than 100,000, and
(ii) a cyclopolymer of dimethyldiallylammonium chloride and acrylamide having a molecular weight greater than 500,000.

2. The process of claim 1 wherein said composition contains from 0.1 to 2 percent by weight of said cationic polymer.
3. The process of claim 1 wherein said composition also contains at least one additional cationic polymer in an amount between 0.1 and 3 percent by weight thereof.
4. The process of claim 1 which also includes permitting said composition after application to said nail surface to act thereon for a period of time ranging from a few minutes to several hours.
5. An oil-in-water emulsion for the reinforcement of fragile or brittle nails consisting essentially of water, an oil phase comprising paraffin oil, at least one polyglycerol alkylether having the formula $$RO-[C_2H_3O(CH_2OH)]_{\overline{n}}H$$

wherein R represents a linear or branched alkyl or alkenyl having from 8–22 carbon atoms or a mixture thereof and n is a number lower than or equal to 10, and from 0.1 to 2 percent by weight of at least one cationic polymer selected from the group consisting of
(1) a crosslinked polyamino-polyamide having the formula $$-[OC-R-CO-Z]-$$

wherein
R represents a radical selected from the group consisting of

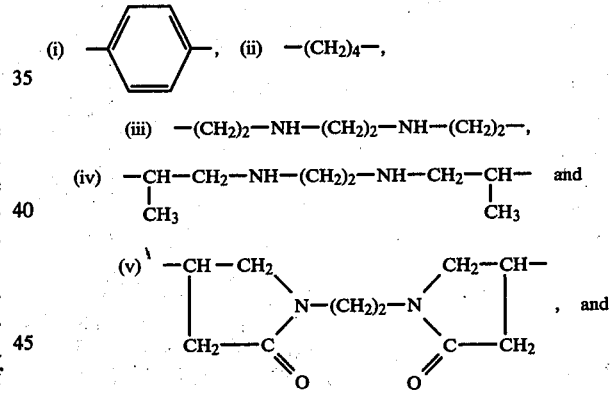

Z represents
(a) in an amount from 60 to 100 mole percent, the radical, $-NH-[(CH_2)_x-NH]_{\overline{n}}$ wherein $x=2$ and $n=2$ or 3, or $x=3$ and $n=2$,
(b) in an amount from 0 to 40 mole percent, a radical selected from the group consisting of:
(a') $-NH-[(CH_2)_x-NH]_{\overline{n}}$ wherein $x=2$ and $n=1$, and
(b')

and
(c) in an amount from 0 to 20 mole percent, the radical, $-NH-(CH_2)_6-NH-$, and crosslinked with a crosslinking agent selected from the group consisting of an epihalohydrin, a diepoxide, a dianhydride and a bis-unsaturated derivative;

(2) an adipic acid-dimethylaminohydroxypropyl diethylenetriamine polymer having a nitrogen content of 17.0–18.0 weight percent thereof, and a viscosity measured in a 30% aqueous solution of 350–800 centipoises at 20° C.;

(3) a polymer obtained by the reaction of a polyalkylene polyamine having two primary amine groups at least one secondary amine group with a dicarboxylic acid selected from the group consisting of diglycolic acid and a saturated aliphatic acid having 3–8 carbon atoms, the molar ratio of said polyalkylene polyamine to said dicarboxylic acid being about 0.8:1 to 1.4:1 and by the reaction of the resulting polyaminoamide with epichlorohydrin, the molar ratio of said epichlorohydrin to the secondary amine group of said polyaminoamide being from 0.5:1 to 1.8:1; and (4) a cyclopolymer selected from the group consisting of
  (i) a homopolymer of dimethyldiallylammonium chloride having a molecular weight lower than 100,000, and
  (ii) a cyclopolymer of dimethyldiallylammonium chloride with acrylamide having a molecular weight greater than 500,000.

6. The composition of claim 5 wherein, based on the total weight of said composition, said paraffin oil is present in an amount between 5 and 20 weight percent and said polyglycerol alkylether is present in an amount between 2 and 20 weight percent.

7. The composition of claim 5 which also includes at least one additional cationic polymer in an amount between 0.1 and 3 weight percent.

8. The composition of claim 5 which also includes an effective amount of a plasticizing agent selected from the group consisting of polyethyleneglycol, isopropyl myristate, 2-octyl dodecanol and butyl stearate.

9. A dispersion in water for reinforcing fragile or brittle nails consisting essentially of water, an effective amount of at least one fatty alcohol selected from the group consisting of (a) cetyl alcohol, (b) steryl alcohol, (c) cetyl stearyl alcohol, and (d) at least one of (a), (b) and (c) oxyethylenated with 20–50 moles of ethylene oxide, and 0.1 to 2 weight percent of at least one cationic polymer selected from the group consisting of (1) a crosslinked polyamino-polyamide having the formula $$+OC-R-CO-Z+$$

wherein
R represents a radical selected from the group consisting of (i) 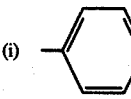, (ii) $-(CH_2)_4-$, (iii) $-(CH_2)_2-NH-(CH_2)_2-NH-(CH_2)_2-$, (iv) $-CH-CH_2-NH-(CH_2)_2-NH-CH_2-CH-$ and
      $\quad\;|$                                      $\;\;|$
      $\;CH_3$                                      $CH_3$ -continued (v) 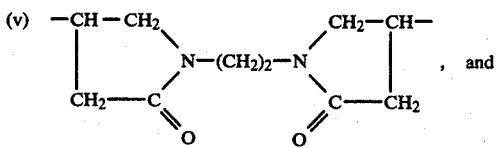, and Z represents (a) in an amount from 60 to 100 mole percent, the radical, $-NH+(CH_2)_x-NH\overline{]_n}$ wherein $x=2$ and $n=2$ on 3, or $x=3$ and $n=2$, (b) in an amount from 0 to 40 mole percent, a radical selected from the group consisting of:

(a') $-NH+(CH_2)_x-NH\overline{]_n}$ wherein $x=2$ and $n=1$, and (b')

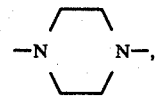

and (c) in an amount from 0 to 20 mole percent, the radical, $-NH-(CH_2)_6-NH-$, and crosslinked with a crosslinking agent selected from the group consisting of an epihalohydrin, a diepoxide, a dianhydride and a bis-unsaturated derivative;

(2) an adipic acid-dimethylaminohydroxypropyl diethylenetriamine polymer having a nitrogen content of 17.0–18.0 weight percent thereof, and a viscosity measured in a 30% aqueous solution of 350–800 centipoises at 20° C.;

(3) a polymer obtained by the reaction of a polyalkylene polyamine having two primary amine groups and at least one secondary amine group with a dicarboxylic acid selected from the group consisting of diglycolic acid and a saturated aliphatic acid having 3–8 carbon atoms, the molar ratio of said polyalkylene polyamine to said dicarboxylic acid being about 0.8:1 to 1.4:1 and by the reaction of the resulting polyaminoamide with epichlorohydrin, the molar ratio of said epichlorohydrin to the secondary amine group of said polyaminoamide being from 0.5:1 to 1.8:1; and (4) a cyclopolymer selected from the group consisting of
  (i) a homopolymer of dimethyldiallylammonium chloride having a molecular weight lower than 100,000, and
  (ii) a cyclopolymer of dimethyldiallylammonium chloride with acrylamide having a molecular weight greater than 500,000.

10. The composition of claim 9 wherein said fatty alcohol is present in an amount between 1 and 10 weight percent based on the total weight of said composition.

11. The composition of claim 9 which also includes at least one additional cationic polymer in an amount between 0.1 and 3 weight percent.

12. The composition of claim 9 which also includes an effective amount of a plasticizing agent selected from the group consisting of polyethylene glycol, isopropyl myristate, 2-octyl dodecanol and butyl stearate.

13. A process for reinforcing fragile or brittle nails comprising applying to the nail surface an effective amount of a composition consisting essentially of an adipic aciddimethylaminohydroxypropyl diethylenetriamine polymer having a nitrogen content of 17.0–18.0 weight percent thereof, and a viscosity measured in a 30% aqueous solution of 350–800 centipoises at 20° C.

14. A process for reinforcing fragile or brittle nails comprising applying to the nail surface an effective amount of a composition consisting essentially of a cyclopolymer selected from the group consisting of
 (i) a homopolymer of dimethyldiallylammonium chloride having a molecular weight lower than 100,000, and
 (ii) a cyclopolymer of dimethyldiallylammonium chloride and acrylamide having a molecular weight greater than 500,000.

15. An oil-in-water emulsion for the reinforcement of fragile or brittle nails consisting essentially of water, an oil phase comprising paraffin oil, at least one polyglycerol alkyl ether having the formula $$RO-[C_2H_3O(CH_2OH)]_nH$$

wherein R represents linear or branched alkyl or alkenyl having 8–22 carbon atoms or a mixture thereof and n is a number lower than or equal to 10, and from 0.1 to 2 percent by weight of, as a cationic polymer, an adipic acid-dimethylaminohydroxypropyl diethylenetriamine polymer having a nitrogen content of 17.0–18.0 weight percent thereof, and a viscosity measured in a 30% aqueous solution of 350–800 centipoises at 20° C.

16. An oil-in-water emulsion for the reinforcement of fragile or brittle nails consisting essentially of water, an oil phase comprising paraffin oil, at least one polyglycerol alkyl ether having the formula $$RO-[C_2H_3O(CH_2OH)]_nH$$

wherein R represents linear or branched alkyl or alkenyl having 8–22 carbon atoms or a mixture thereof and n is a number lower than or equal to 10, and from 0.1 to 2 percent by weight of, as a cationic polymer, a cyclopolymer selected from the group consisting of
 (i) a homopolymer of dimethyldiallylammonium chloride having a molecular weight lower than 100,000, and
 (ii) a cyclopolymer of dimethyldiallylammonium chloride and acrylamide having a molecular weight greater than 500,000.

17. A dispersion in water for reinforcing fragile or brittle nails consisting essentially of water, an effective amount of at least one fatty alcohol selected from the group consisting of (a) cetyl alcohol, (b) stearyl alcohol, (c) cetyl stearyl alcohol, and (d) at least one of (a), (b) and (c) oxyethylenated with 20–50 moles of ethylene oxide, and 0.1 to 2 weight percent of, as a cationic polymer, an adipic acid-dimethylaminohydroxypropyl diethylenetriamine polymer having a nitrogen content of 17.0–18.0 weight percent thereof, and a viscosity measured in a 30% aqueous solution of 350–800 centipoises at 20° C.

18. A dispersion in water for reinforcing fragile or brittle nails consisting essentially of water, an effective amount of at least one fatty alcohol selected from the group consisting of (a) cetyl alcohol, (b) stearyl alcohol, (c) cetyl stearyl alcohol, and (d) at least one of (a), (b) and (c) oxyethylenated with 20–50 moles of ethylene oxide, and 0.1 to 2 weight percent of, as a cationic polymer, a cyclopolymer selected from the group consisting of
 (i) a homopolymer of dimethyldiallylammonium chloride having a molecular weight lower than 100,000 and
 (ii) a cyclopolymer of dimethyldiallylammonium chloride and acrylamide having a molecular weight greater than 500,000.

19. A oil-in-water emulsion for the reinforcement of fragile or brittle nails consisting essentially of water, an oil phase comprising paraffin oil, at least one polyglycerol alkyl ether having the formula $$RO-C_2H_3O(CH_2OH)]_nH$$

wherein R represents a linear or branched alkyl or alkenyl having from 8–22 carbon atoms or a mixture thereof and n is a number lower than or equal to 10, and from 0.1 to 2 percent by weight of, as a cationic polymer, a polyaminoamide of adipic acid and diethylene triamine crosslinked with epichlorohydrin in an amount of 11 moles of epichlorohydrin per 100 amine groups of said diethylene triamine.

20. The oil-in-water emulsion of claim 19 wherein said polyglycerol alkyl ether is a mixture of
 (a) $C_{16}H_{33}/C_{18}H_{37}-O-C_2H_3O(CH_2OH)]_6H$, and
 (b) $C_{16}H_{33}/C_{18}H_{37}-O-C_2H_3O(CH_2OH)]_2H$.

21. A dispersion in water for reinforcing fragile or brittle nails consisting essentially of water, an effective amount of at least one fatty alcohol selected from the group consisting of (a) cetyl alcohol, (b) stearyl alcohol, (c) cetyl stearyl alcohol, and (d) at least one of (a), (b) and (c) oxyethylenated with 20–50 moles of ethylene oxide, and 0.1 to 2 weight percent of, as a cationic polymer, a polyaminoamide of adipic acid and diethylene triamine crosslinked with epichlorohydrin in an amount of 11 moles of epichlorohydrin per 100 amine groups of said diethylene triamine.

22. The dispersion of claim 21 wherein said fatty alcohol is present in an amount of 1 to 10 weight percent based on the total weight of said dispersion.

23. The dispersion of claim 21 wherein said fatty alcohol is cetyl stearyl alcohol.

24. An oil-in-water emulsion for the reinforcement of fragile or brittle nails consisting of water, an oil phase comprising paraffin oil, at least one polyglycerol alkylether having the formula $$RO-[C_2H_3O(CH_2OH)]_nH$$

wherein R represents a linear or branched alkyl or alkenyl having from 8–22 carbon atoms or a mixture thereof and n is a number lower than or equal to 10, and from 0.1 to 2 percent by weight of at least one cationic polymer selected from the group consisting of
 (1) a crosslinked polyamino-polyamide having the formula $$-[OC-R-CO-Z]-$$

wherein
 R represents a radical selected from the group consisting of (i) , (ii) $-(CH_2)_4-$, (iii) $-(CH_2)_2-NH-(CH_2)_2-NH-(CH_2)_2-$, -continued (iv) 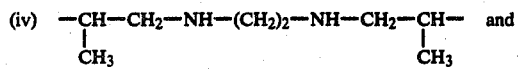

(v) 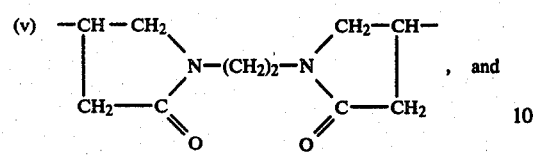

Z represents
(a) in an amount from 60 to 100 mole percent, the radical, $-NH+(CH_2)_x-NH]_{\overline{n}}$ wherein x=2 and n=2 or 3, or x=3 and n=2,
(b) in an amount from 0 to 40 mole percent, a radical selected from the group consisting of:
  (a') $-NH-(CH_2)_x-NH]_n$ wherein x=2 and n=1, and
  (b')

and
(c) in an amount from 0 to 20 mole percent, the radical, $-NH-(CH_2)_6-NH-$, and crosslinked with a crosslinking agent selected from the group consisting of an epihalohydrin, a diepoxide, a dianhydride and a bis-unsaturated derivative;

(2) an adipic acid-dimethylaminohydroxypropyl diethylenetriamine polymer having a nitrogen content of 17.0–18.0 weight percent thereof, and a viscosity measured in a 30% aqueous solution of 350–800 centipoises at 20° C.;

(3) a polymer obtained by the reaction of a polyalkylene polyamine having two primary amine groups at least one secondary amine group with a dicarboxylic acid selected from the group consisting of diglycolic acid and a saturated aliphatic acid having 3–8 carbon atoms, the molar ratio of said polyalkylene polyamine to said dicarboxylic acid being about 0.8:1 to 1.4:1 and by the reaction of the resulting polyaminoamide with epichlorohydrin, the molar ratio of said epichlorohydrin to the secondary amine group of said polyaminoamide being from 0.5:1 to 1.8:1; and (4) a cyclopolymer selected from the group consisting of
  (i) a homopolymer of dimethyldiallylammonium chloride having a molecular weight lower than 100,000, and
  (ii) a cyclopolymer of dimethyldiallylammonium chloride with acrylamide having a molecular weight greater than 500,000.

* * * * *